(12) United States Patent
Qian

(10) Patent No.: US 9,839,739 B2
(45) Date of Patent: Dec. 12, 2017

(54) SURGICAL IRRIGATION AND SUCTION APPARATUS

(71) Applicant: Jianmin Qian, Wuxi (CN)

(72) Inventor: Jianmin Qian, Wuxi (CN)

( * ) Notice: Subject to any disclaimer, the term of this patent is extended or adjusted under 35 U.S.C. 154(b) by 340 days.

(21) Appl. No.: 14/579,830

(22) Filed: Dec. 22, 2014

(65) Prior Publication Data

US 2015/0335813 A1   Nov. 26, 2015

(30) Foreign Application Priority Data

May 22, 2014   (CN) .......................... 2014 1 0216879

(51) Int. Cl.
*A61M 1/00* (2006.01)
*A61M 1/06* (2006.01)
*A61M 3/02* (2006.01)

(52) U.S. Cl.
CPC .......... *A61M 3/0283* (2013.01); *A61M 3/022* (2014.02); *A61M 2205/3334* (2013.01); *A61M 2210/1021* (2013.01)

(58) Field of Classification Search
CPC .. A61M 2205/3334; A61M 2210/1021; A61M 3/022; A61M 3/0283
See application file for complete search history.

(56) References Cited

U.S. PATENT DOCUMENTS

| | | | | |
|---|---|---|---|---|
| 5,295,956 | A | * | 3/1994 | Bales .................. A61M 1/0045 604/119 |
| 2014/0207056 | A1 | * | 7/2014 | Bono .................. A61M 3/0283 604/34 |
| 2015/0217041 | A1 | * | 8/2015 | Monty ................ A61M 3/0262 604/153 |

* cited by examiner

*Primary Examiner* — Rebecca E Eisenberg
(74) *Attorney, Agent, or Firm* — Morgan, Lewis & Bockius LLP

(57) ABSTRACT

A surgical irrigation and suction apparatus includes a housing forming a handle and a barrel. The housing contains a suction tube for disposing of waste slurry and am irrigation tube for provision of irrigation fluid. The apparatus further includes a removable tube divided into an irrigation chamber and a suction chamber. The two chambers are collinearly arranged with respect to each other. The removable tube is coupled with the housing via a tube fitting. The apparatus further includes an inlet/outlet tip coupled with the other end of the removable tube, the tip including an outlet port and a plurality of inlet ports, respectively. The irrigation chamber terminates distal to the barrel with the tip arranged to spray the irrigation fluid through the outlet port. The suction chamber terminates distal to the barrel with the tip for recovery of the waste slurry through the plurality of inlet ports.

17 Claims, 5 Drawing Sheets

SURGICAL IRRIGATION AND SUCTION APPARATUS

RELATED APPLICATION

This application claims priority to Chinese Patent Application No. 201410216879.3, entitled "MULTIPURPOSE SURGICAL IRRIGATION AND SUCTION APPARATUS", filed on May 22, 2014, which is incorporated by reference in its entirety.

TECHNICAL FIELD

The disclosed embodiments relate to medical devices, and in particular, to an irrigation and suction apparatus for use in surgical procedures.

BACKGROUND

Surgical irrigation apparatus and surgical suction apparatus are routinely used in surgical procedures to clean wounds and remove surgical debris, such as, blood, irrigation fluids (e.g., solutions), and/or fragments of soft and hard (e.g. bone) tissue. Several problems, however, are present with conventional apparatus for irrigation and suction. For one, such apparatuses are often separate ones and used separately. For example, a surgeon will spray an area with an irrigator and then exchange the irrigator for a suction device in order to remove the debris. This represents an unnecessary degree of inconvenience for the surgeon. Secondly, conventional apparatus typically do not provide convenient control mechanisms for modifying the strength of the suction and/or irrigation.

SUMMARY

Accordingly, there is a need for one combined apparatus that conveniently provide irrigation fluids (e.g., water or saline solution) and suction of waste slurry (e.g., a mixture of water, blood, solid debris, and/or other bodily fluids) during the course of surgical procedures. To that end, in accordance with some embodiments, a combined surgical irrigation and suction apparatus is provided. The surgical irrigation and suction apparatus includes a hollow housing forming a handle and a barrel. The hollow housing contains a suction tube for disposing of waste slurry and an irrigation tube for provision of irrigation fluid. The surgical irrigation and suction apparatus further includes a removable tube divided into an irrigation chamber and a suction chamber by a separator within the removable tube along a longitudinal direction of the removable tube. The two chambers are collinearly arranged with respect to each other. The removable tube is coupled with the hollow housing via a tube fitting such that the suction chamber is coupled with the suction tube to form a suction conduit for transporting the waste slurry and the irrigation chamber is coupled with the irrigation tube to form an irrigation conduit for transporting the irrigation fluid. The surgical irrigation and suction apparatus further includes an inlet/outlet tip coupled with the removable tube. The inlet/outlet tip includes an outlet port and a plurality of inlet ports, respectively. The irrigation chamber terminates distal to the barrel with the inlet/outlet tip arranged to spray the irrigation fluid through the outlet port substantially collinearly with respect to a distal end of the irrigation chamber. The suction chamber terminates distal to the barrel with the inlet/outlet tip for recovery of the waste slurry through the plurality of inlet ports.

In some embodiments, the flow of the irrigation fluid through the irrigation tube and the flow of the waste slurry through the suction tube are independently controllable via thumb actuation of a respective pinch valve corresponding to each of the irrigation tube and the suction tube, respectively.

In some embodiments, each of the respective pinch valves corresponding to the irrigation tube and the suction tube is configured to adjust the corresponding flow through a movement relative to the hollow housing. The movement further includes a translation of the pinch valve and a rotation of the pinch valve relative to the hollow housing.

In some embodiments, each of the respective pinch valves corresponding to the irrigation tube and the suction tube, respectively, includes a plurality of discrete flow settings and a setting that entirely shuts off flow to the respective tube.

In some embodiments, the suction chamber and the irrigation chamber form a single rigid partitioned tube comprising the removable tube. In some embodiments, the single rigid partitioned tube is formed from a single extruded or molded piece of plastic.

In some embodiments, the surgical irrigation and suction apparatus is disposable.

In some embodiments, the surgical irrigation and suction apparatus is for use in abdominal surgery.

In some embodiments, the handle of the hollow housing allows a surgeon's hand to grasp the surgical irrigation and suction apparatus so as to manipulate the directionality of the irrigation fluid and the intake of the waste slurry.

In some embodiments, at least one of the respective inlet ports for recovery of the waste slurry is arranged to produce flow substantially collinear with respect to a distal end of the suction chamber. In addition, at least one of the respective inlet ports for recovery of the waste slurry is arranged to produce flow substantially perpendicular with respect to the distal end of the suction chamber.

In some embodiments, the surgical irrigation and suction apparatus further includes an irrigation inlet port for coupling the irrigation tube with a source of pressurized irrigation fluid and a suction outlet port for coupling the suction tube with an external suction pump to collect the waste slurry.

In some embodiments, the irrigation inlet port and the suction outlet port are housed in or mounted on the handle of the hollow housing.

In some embodiments, the removable tube is between ten and twenty-five centimeters (cm) in length.

In some embodiments, the hollow housing comprises two molded pieces of plastic, each forming half of the housing and coupled with one another.

In some embodiments, the tube fitting is a barbed Wye ("Y") tube fitting partitioned into two branches so as to keep the irrigation fluid from the irrigation chamber separate from the waste flurry from the suction chamber.

In some embodiments, the removable tube is divided unevenly into the irrigation chamber and the suction chamber by the separator within the tube along the longitudinal direction of the removable tube such that the irrigation chamber is smaller than the suction chamber.

BRIEF DESCRIPTION OF THE DRAWINGS

Like reference numerals refer to corresponding parts throughout the drawings.

DETAILED DESCRIPTION OF EMBODIMENTS

Described below are a combined surgical irrigation and suction apparatus that allow a surgeon to clean and clear wounds and surgical sites with an added level of convenience and control. For example, a surgical irrigation and suction apparatus is provided that is lightweight and shaped like a gun so that the surgeon can easily grasp, manipulate, and direct the spray or irrigation and/or the suction. In addition, the strength of both the irrigation spray and the suction are independently controllable by the surgeon's thumb without changing her grip on the apparatus. The irrigation spray and/or suction are applied to the patient via a removable tube. In some embodiments, the removable tube is long enough to reach down, e.g., to within a patient's abdominal cavity (e.g., the surgical irrigation and suction apparatus is for use in abdominal surgery). The removable tube is partitioned into separate chambers for irrigation fluid and waste slurry (e.g., debris) and terminated with a tip having an outlet port designed to provide a reliable and directed spray of irrigation fluid and a plurality of inlet ports for recovery of the waste slurry. The plurality of inlet ports is designed to provide quick diffuse suction and avoid clogs.

Reference will now be made in detail to various implementations, examples of which are illustrated in the accompanying drawings. In the following detailed description, numerous specific details are set forth in order to provide a thorough understanding of the present disclosure and the described implementations herein. However, implementations described herein may be practiced without these specific details. In other instances, well-known methods, procedures, components, and mechanical apparatus have not been described in detail so as not to unnecessarily obscure aspects of the implementations.

Figure 1:
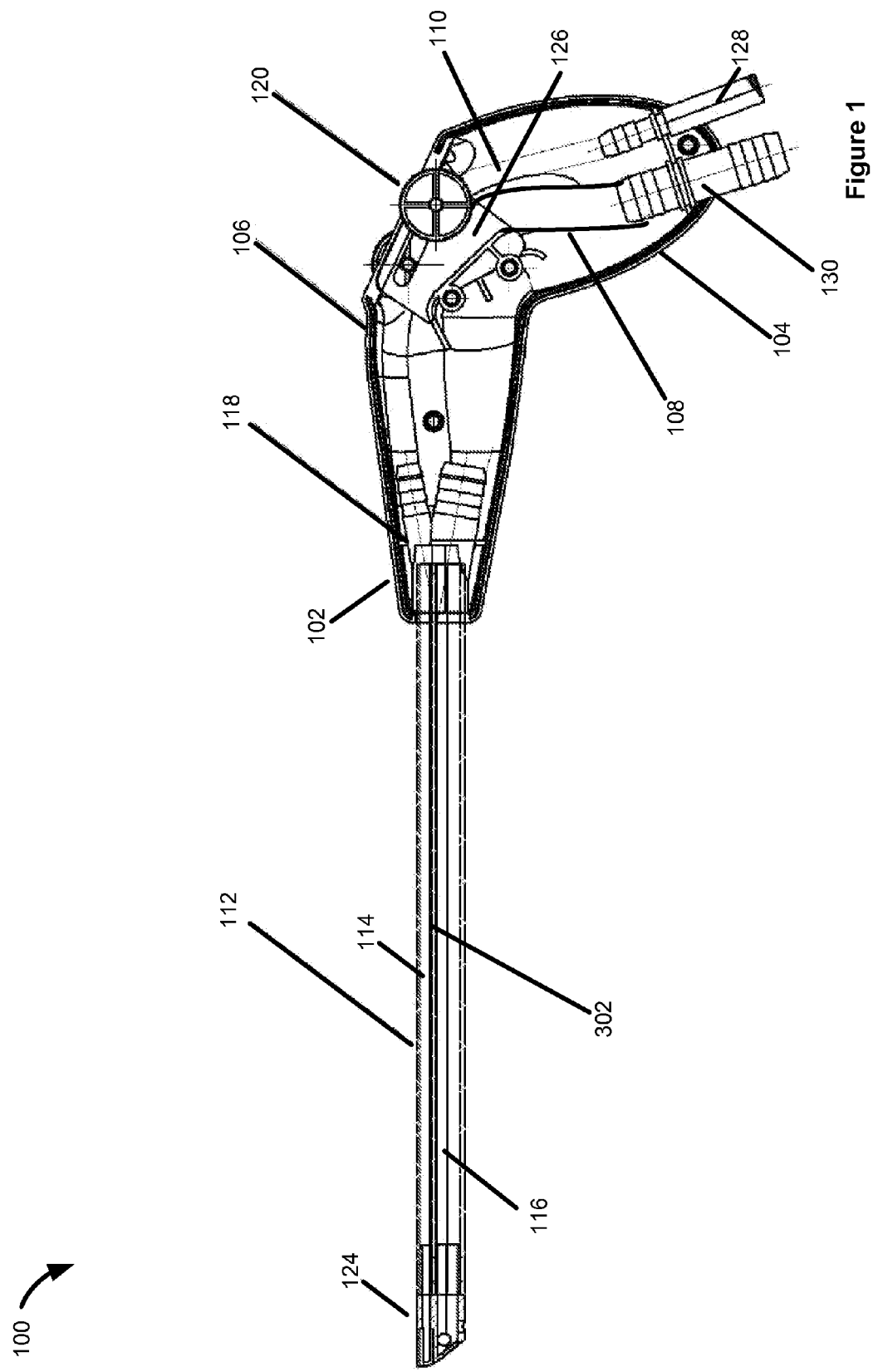
FIG. 1 is a cross-sectional view of a surgical irrigation and suction apparatus, in accordance with some embodiments.

FIG. 1 is a cross-sectional view of a surgical irrigation and suction apparatus 100, in accordance with some embodiments. In some embodiments, the surgical irrigation and suction apparatus 100 is disposable. The surgical irrigation and suction apparatus 100 includes a hollow housing 102 forming a handle 104 and a barrel 106. The hollow housing contains a suction tube 108 for disposing of waste slurry (e.g., surgical debris, such as, blood, waste irrigation fluids and/or fragments of soft and hard tissue) and an irrigation tube 110 for provision of irrigation fluid (e.g., irrigation solutions such as normal saline solution, bacitracin solution, castile soap, and benzalkonium chloride). Irrigation tube 110 provides fresh irrigation fluids from a pump (not shown) coupled with a reservoir of irrigation fluid (e.g., a saline bag, not shown). In some embodiments, suction tube 108 and irrigation tube 110 are soft tubes (e.g., made of a material having a Shore hardness less than A75).

Surgical irrigation and suction apparatus 100 also includes a removable tube 112 divided into an irrigation chamber 114 and a suction chamber 116 by a separator 302 within the tube along a longitudinal direction of the tube. Irrigation chamber 114, suction chamber 116, and the separate are shown more clearly in FIGS. 2-5. The two chambers (i.e., irrigation chamber 114 and suction chamber 116) are collinearly arranged with respect to each other (e.g., they are substantially parallel to each other in a side-by-side or co-axial arrangement). In some embodiments, removable tube 112 has a substantially circular cross-section and the separator 302 is, geometrically speaking, a chord of the circular cross-section of removable tube 112. Thus, in some embodiments, the respective cross-sections of irrigation chamber 114 and suction chamber 116 are, geometrically speaking, segments of a circular cross-section of removable tube 112.

Removable tube 112 is coupled with hollow housing 102 such that the suction chamber 116 is coupled with the suction tube 108 to form a suction conduit for transporting the waste slurry and the irrigation chamber 114 is coupled with the irrigation tube 110 to form an irrigation conduit for transporting the irrigation fluid (e.g., fresh, sterile, and/or unused irrigation fluid). In some embodiments, the coupling is achieved by a tube fitting 118 having a first end that connects to suction tube 108 and a second end that connects to irrigation tube 110. In some embodiments, tube fitting 118 is a barbed Wye ("Y") tube fitting (e.g., having first and second barbed male ends that connect, respectively, to the suction tube 108 and the irrigation tube 110). In some embodiments, tube fitting 118 is constructed from nylon or another plastic and is design to be connected to polyvinyl chloride (PVC) or polyurethane tubing. In some embodiments, tube fitting 118 is capable of being sterilized (e.g., by an autoclave). In some embodiments, tube fitting 118 is partitioned into two branches to keep fluids from the irrigation tube 110 separate from fluids from the suction tube 108.

The distal end of the removable tube 112 relative to barrel 106 is coupled with an inlet/outlet tip 124 including an outlet port and a plurality of inlet ports. The irrigation chamber terminates distal to barrel 106 with the outlet port of the tip 124 arranged to spray the irrigation fluid through the outlet port substantially collinearly with respect to a distal end of the irrigation chamber, as described in more detail with reference to FIG. 5. The suction chamber terminates distal to barrel 106 with the plurality of inlet ports for recovery of the waste slurry through the inlet ports and is also described in greater detail with reference to FIG. 5.

In some embodiments, flow of the irrigation fluid through irrigation tube 110 and flow of the waste slurry through suction tube 108 are independently controllable via thumb actuation of a respective pinch valve 120 corresponding to each of the irrigation tube and the suction tube, respectively (only one of which is shown from the view in FIG. 1). In some embodiments, each of the respective pinch valves corresponding to the irrigation tube and the suction tube is configured to adjust the corresponding flow through a movement relative to the hollow housing. For example (as shown in FIG. 1), the pinch valve 120 is in the shape of a wheel having an axis confined within a groove. The surgeon may rotate the pinch valve 120 using her thumb to force the wheel's axis to move along the groove. In other words, the movement of the pinch valve 120 includes a translation of the axis and a rotation of the wheel relative to the hollow housing. The relative position of the axis within the groove determines the opening of the corresponding tube for transporting the fluid within. In some embodiments, each of the respective pinch valves 120 corresponding to the irrigation tube and the suction tube, respectively, includes a plurality of discrete flow settings and a setting that entirely shuts off flow to the respective tube. For example, in some embodiments, a pinch valve 120 includes a wheel and a slanted plate. The wheel is situated with its axle along a linear guide such that it can be pushed forward by a surgeon's thumb. A series of teeth along the linear guide engage the axle so that the wheel can be seated at discrete intervals along the linear guide without continuing to apply thumb pressure. The tube is disposed in a space 126 between the wheel and the slanted plate such that as the wheel is pushed forward by the surgeon's thumb, the tube (e.g., being soft, as noted above) is further constricted (for clarity, the drawing of suction tube 104 is omitted from space 126, however, in some embodiments, suction tube 104 passes through space 126).

This design allows the surgeon to conveniently control the flow independently through both the suction tube 104 and irrigation tube 110. Such features are convenient because, for example, a surgeon may want to irrigate an area aggressively (e.g., with a high flow rate), shut off or slow the irrigation, and suction the area to remove waste slurry. The design described above allows a surgeon to do so with only minimal manipulation of his thumb. In some embodiments, rather than being controllable via the surgeon's thumb, the pinch valves are controllable using the surgeon's index finger (e.g., the wheels of the pinch valves are on the underside of barrel 106. In some embodiments, a different kind of control mechanism (i.e., other than the wheel-actuated pinch valve mechanism described above), is used to control the flow through the respective tubes.

In some embodiments, removable tube 112 is rigid. In some embodiments, handle 104 of hollow housing 102 allows a surgeon's hand to grasp the surgical irrigation and suction apparatus 100 so as to manipulate the directionality of the irrigation fluid and the intake of the waste slurry (e.g., by pointing the rigid tube). Thus, the flow rate and direction of irrigation fluid, as wells the flow rate and location of intake of waste slurry, are easily controlled with slight manipulations of one of the surgeon's hands.

In some embodiments, surgical irrigation and suction apparatus 100 includes an irrigation inlet port 128 for coupling irrigation tube 110 with a source of pressurized irrigation fluid (e.g., via another tube running to a pump connected to a bag of irrigation fluid). Surgical irrigation and suction apparatus 100 includes a suction outlet port 130 for coupling suction tube 108 with an external suction pump to collect the waste slurry (e.g., via another tube). One or both of irrigation inlet port 128 and suction outlet port 130 are, in some embodiments, barbed tube couplings. In some embodiments, irrigation inlet port 128 and suction outlet port 130 are housed in or mounted on the handle 104 of hollow housing 102.

Figure 2:
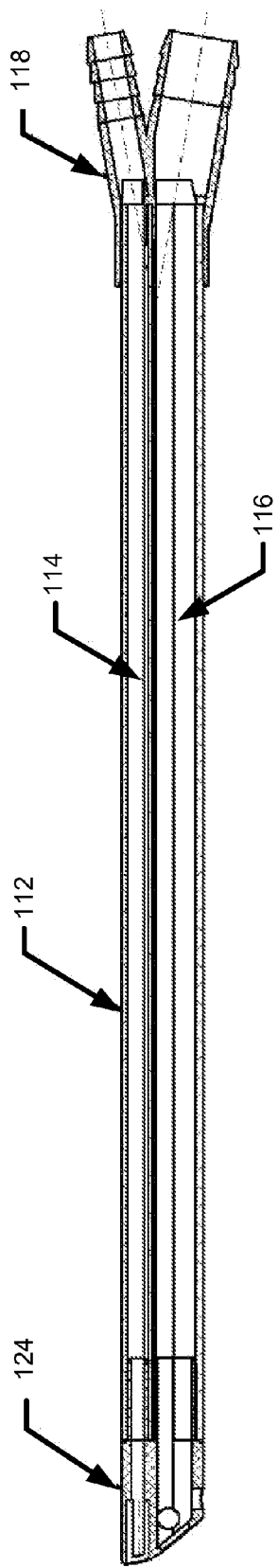
FIG. 2 is a longitudinal cross-sectional view of a removable tube divided into an irrigation chamber and a suction chamber, in accordance with some embodiments.

FIG. 2 is a longitudinal cross-sectional view of a removable tube 112 divided into an irrigation chamber 114 and a suction chamber 116, in accordance with some embodiments. In some embodiments, suction chamber 116 and irrigation chamber 114 form a single rigid partitioned tube comprising removable tube 112 (e.g., removable tube 112 is a rigid tube). In some embodiments, removable tube 112 is made of a plastic material that can be autoclaved (e.g., withstand the heat and environment of an autoclave). In this manner, removable tube 112 can be sterilized. In some embodiments, hollow housing 102 (FIG. 1) and some or all of its interior components are non-disposable and removable tube 112 is a disposable tip. Alternatively, in some embodiments, the entirety of surgical irrigation and suction apparatus 100 (FIG. 1) is disposable.

In some embodiments, removable tube 112 comes in a variety of lengths. For example, the same surgical irrigation and suction apparatus 100 (FIG. 1) may be configured to attach to a removable tube 112 having a length of 2-5 cm, 5-10 cm, and/or 10-25 cm. By providing removable tubes 112 in a variety of lengths, surgical irrigation and suction apparatus 100 (FIG. 1) is useful for a variety of types of surgeries. For example, a longer (e.g., 10-25 cm) removable tube may be necessary, or at least more convenient, for abdominal surgeries where surgical sites are farther away from a patient's incision. On the other hand, when irrigation is desired closer to a patient's incision, a longer tube could be unwieldy and inaccurate. Thus, in some circumstances, the longer tube can be swapped out for a shorter tube (e.g., a removable tube 112 between 2-5 cm in length).

As an alternative to a removable tube, in some embodiments, surgical irrigation and suction apparatus 100 terminates in a tube that is analogous to removable tube 112 except for the fact it the tube is not removable.

Figure 3:
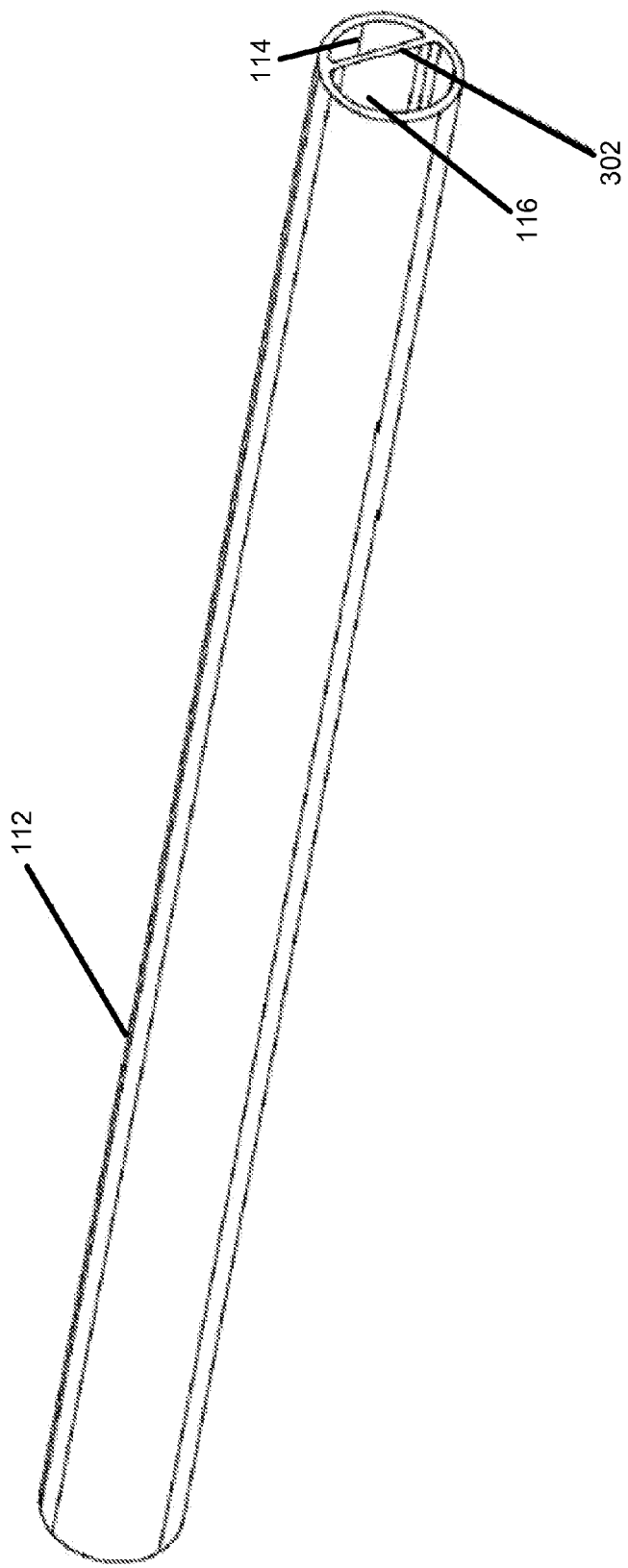
FIG. 3 is a perspective view of a removable tube divided into an irrigation chamber and a suction chamber, in accordance with some embodiments.
Figure 4:
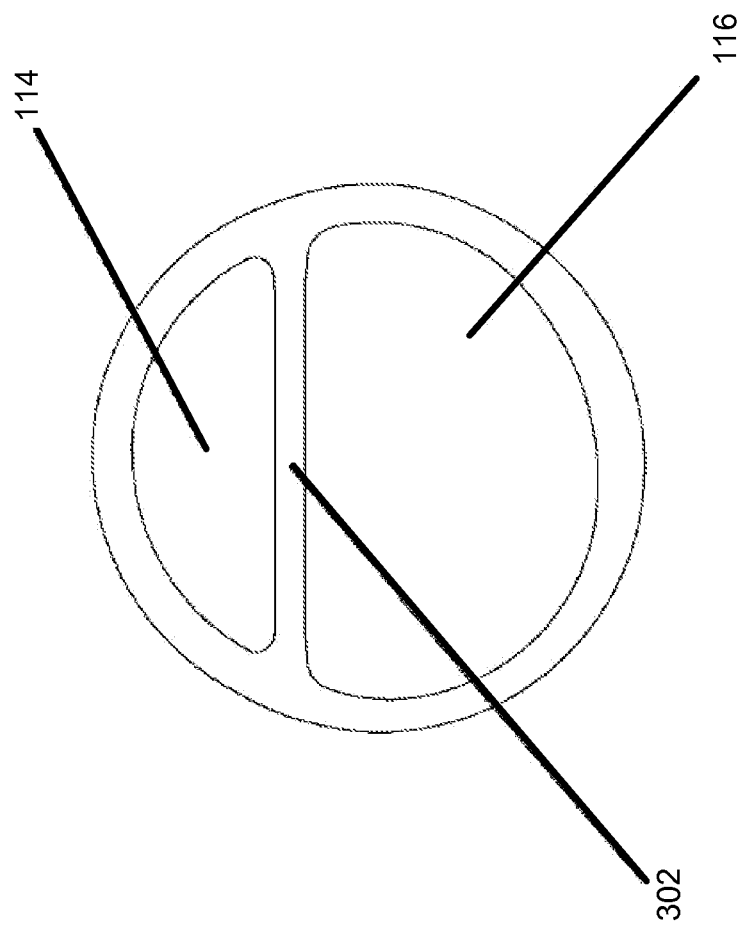
FIG. 4 is a transverse cross-sectional view of a removable tube divided into an irrigation chamber and a suction chamber, in accordance with some embodiments.

FIG. 3 is a perspective view of a removable tube 112 divided into an irrigation chamber 114 and a suction chamber 116, in accordance with some embodiments. FIG. 4 is a transverse cross-sectional view of removable tube 112, in accordance with some embodiments. Removable tube 112 divided into an irrigation chamber 114 and a suction chamber 116 by a separator 302 within removable tube 112 along a longitudinal direction of removable tube 112. The two chambers (i.e., irrigation chamber 114 and suction chamber 116) are collinearly arranged with respect to each other (e.g., they are substantially parallel to each other in a side-by-side or co-axial arrangement). In some embodiments, removable tube 112 has a substantially circular cross-section (e.g., the transverse cross-sections, conceptually sliced through the long axes of removable tube 112). In this case, separator 302 is, geometrically speaking, a chord of (e.g., a straight line across) the circular cross-section of removable tube 112. Thus, in some embodiments, the respective cross-sections of irrigation chamber 114 and suction chamber 116 are, geometrically speaking, segments of cross-section of the removable tube 112. In some embodiments, the separator forms a chord of the circular cross-section that is less than the diameter of the circular cross-section, thus dividing the circular cross-section into two unevenly (e.g., asymmetrical) chambers. In some embodiments, since the irrigation fluid is generally a clean, non-viscous fluid, the irrigation chamber 114 carrying the irrigation fluid is the smaller of the two chambers formed by the asymmetry. Since waste slurry is generally more viscous and has solid particles, suction chamber 116 is the larger of the two chambers formed by the asymmetry.

As noted above, in some embodiments, suction chamber 116 and irrigation chamber 114 form a single rigid partitioned tube comprising removable tube 112. Moreover, the single rigid partitioned tube is formed from a single extruded or molded piece of plastic.

Figure 5:
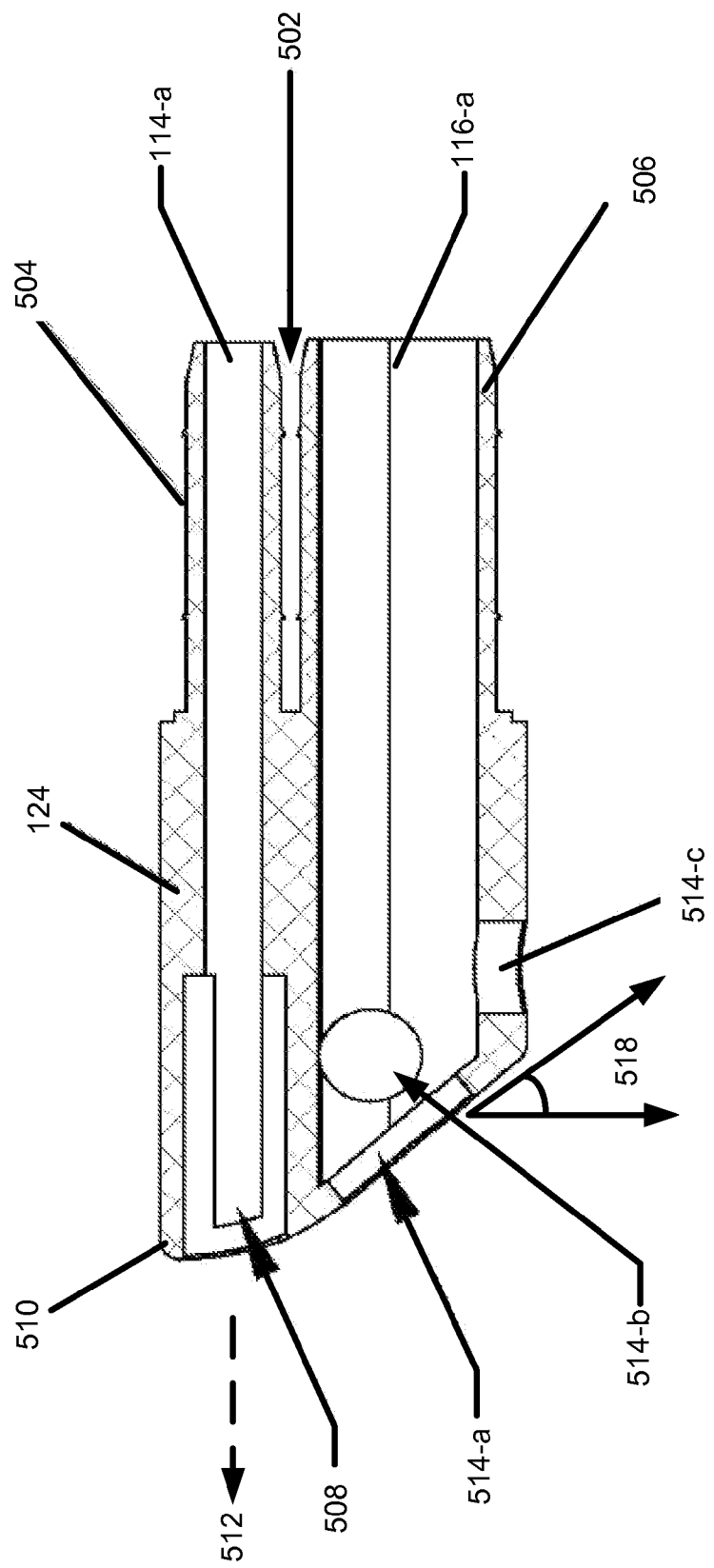
FIG. 5 is a longitudinal cross-sectional view of a tip that terminates the removable tube of FIGS. 2-4, in accordance with some embodiments.

FIG. 5 is a longitudinal cross-section view of tip 124 that terminates the removable tube 112 of FIGS. 2-4, in accordance with some embodiments. Tip 124 is shown in a broad context of surgical irrigation and suction apparatus 100 in FIG. 1. In some embodiments, as described in greater detail below, tip 124 is manufactured separately (e.g., is a distinct part) from removable tube 112 (FIGS. 2-4). To that end, in some embodiments, tip 124 is configured to fit on, or within, or engage with, removable tube 112 (FIGS. 2-4). A particular example of a mechanism for attaching tip 124 to removable tube 124 is by clip 502, shown in FIG. 5. Clip 502 fits snuggly (e.g., in a water tight fashion) over separator 302 (FIG. 3). In some embodiments, clip 502 includes one or more teeth that aid in securing tip 124 to separate 302 of removable tube 112. In some embodiments, clip 502 is further secured to removable tube 112 by use of an adhesive. In some embodiments, tip 124 includes a male fitting 504 that is a negative of irrigation chamber 114 (or substantially a negative of irrigation chamber 114) of removable tube 112 (e.g., fits snuggly within irrigation chamber 114) and a male fitting 506 that is a negative of suction chamber 116 (or substantially a negative of irrigation chamber 114) of removable tube 112 (e.g., fits snuggly within suction chamber 116). In such embodiments, clip 502 is a negative space separating male fitting 504 and male fitting 506. Thus, irrigation chamber 114 is extended with a portion 114-a of tip 124 and suction chamber 116 is extended with a portion 116-a of tip 124.

In some embodiments, tip 124 provides termination of the irrigation chamber 114 and suction chamber 116 that is optimized in a number of ways. For example, in some embodiments, irrigation chamber 114 (more particularly, portion 114-a thereof) terminates distal to barrel 106 (FIG. 1) with an outlet port 508 arranged to spray the irrigation fluid substantially collinearly with respect to a distal end 510 of the irrigation chamber 114 (e.g., the spray is substantially along the axis 512). Outlet port 508 is relatively narrow (e.g., narrower than some or all inlet ports 514, or roughly 2 mm in diameter) producing a jet spray of irrigation liquid capable of providing enough force to dislodge debris, bacteria, and the like from a wound or surgical site. On the other hand, suction chamber 116 terminates distal to the barrel with a plurality of inlet ports 514 for recovery of the waste slurry.

In some embodiments, at least one of the inlet ports 514 for recovery of the waste slurry is arranged to produce flow substantially collinear with respect to a distal end 510 of suction chamber 116 and at least one of the inlet ports 514 for recovery of the waste slurry is arranged to produce flow substantially perpendicular with respect to the distal end 510 of suction chamber 116. Alternatively, in some embodiments, one of the inlet ports 514-a is offset by angle 518 with respect to outlet port 508. This allows the surgeon to maintain a spray of irrigation liquid at angle 518 to a wound or surgical site while positioning inlet port 514 uniformly close to the wound or surgical site. Providing the spray of irrigation fluid at angle 518 with respect to the wound or surgical site (e.g., the surface of the wound or surgical site) results in a horizontal component of the spray's force that is better able to blast away debris and bacteria. Positioning inlet port 514-a uniformly close to the wound or surgical site improves suctioning. Inlet port 514-a is a relatively large bore port, so as to avoid clogging (e.g., 4 mm in diameter).

In addition, in some embodiments, tip 124 includes a plurality of secondary inlet ports (e.g., inlet port 514-b and inlet port 514-c). In some circumstances, secondary inlet ports 514-b and 514-c serve dual purposes. One purpose is providing additional locations for suction, which helps to make the suction more diffuse and less damaging to the tissue at the wound or surgical site being suctioned from (e.g., diffuse suction is less harsh and irritating). The second purpose is to allow for air flow to enter inlet ports 514-b and 514-c while fluid (e.g., waste slurry) is being suctioned through inlet port 514-a. This helps maintain smooth flow through inlet port 514-a in the case where tissue becomes sucked onto inlet port 514-a, thereby acting as its own clog.

While particular embodiments are described above, it will be understood it is not intended to limit the invention to these particular embodiments. On the contrary, the invention includes alternatives, modifications and equivalents that are within the spirit and scope of the appended claims. Numerous specific details are set forth in order to provide a thorough understanding of the subject matter presented herein. But it will be apparent to one of ordinary skill in the art that the subject matter may be practiced without these specific details. In other instances, well-known methods, procedures, components, and circuits have not been described in detail so as not to unnecessarily obscure aspects of the embodiments.

The terminology used in the description of the invention herein is for the purpose of describing particular embodiments only and is not intended to be limiting of the invention. As used in the description of the invention and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "including," "comprises," and/or "comprising," when used in this specification, specify the presence of stated features, operations, elements, and/or components, but do not preclude the presence or addition of one or more other features, operations, elements, components, and/or groups thereof.

As used herein, the term "if" may be construed to mean "when" or "upon" or "in response to determining" or "in accordance with a determination" or "in response to detecting," that a stated condition precedent is true, depending on the context. Similarly, the phrase "if it is determined [that a stated condition precedent is true]" or "if [a stated condition precedent is true]" or "when [a stated condition precedent is true]" may be construed to mean "upon determining" or "in response to determining" or "in accordance with a determination" or "upon detecting" or "in response to detecting" that the stated condition precedent is true, depending on the context.

Although some of the various drawings illustrate a number of logical stages in a particular order, stages that are not order dependent may be reordered and other stages may be combined or broken out. While some reordering or other groupings are specifically mentioned, others will be obvious to those of ordinary skill in the art and so do not present an exhaustive list of alternatives. Moreover, it should be recognized that the stages could be implemented in hardware, firmware, software or any combination thereof.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the invention and its practical applications, to thereby enable others skilled in the art to best utilize the invention and various embodiments with various modifications as are suited to the particular use contemplated.

What is claimed is:

1. A surgical irrigation and suction apparatus, comprising:
 a hollow housing forming a handle and a barrel, wherein the hollow housing contains a suction tube for disposing of waste slurry and an irrigation tube for provision of irrigation fluid;
 a removable tube divided into an irrigation chamber and a suction chamber by a separator within the tube along a longitudinal direction of the removable tube, wherein the two chambers are collinearly arranged with respect to each other with the suction chamber having a larger cross-sectional area than that of the irrigation chamber, and the removable tube is coupled with the hollow housing via a tube fitting such that the suction chamber is coupled with the suction tube to form a suction conduit for transporting waste slurry and the irrigation chamber is coupled with the irrigation tube to form an irrigation conduit for transporting irrigation fluid; and an inlet/outlet tip including two male fittings removably coupled with the irrigation chamber and the suction chamber of the removable tube, wherein the inlet/outlet tip includes an outlet port and a plurality of inlet ports, respectively;

wherein:

the irrigation chamber terminates distal to the barrel with the inlet/outlet tip arranged to spray the irrigation fluid through the outlet port substantially collinearly with respect to a distal end of the irrigation chamber; and the suction chamber terminates distal to the barrel with the inlet/outlet tip for recovery of the waste slurry through the plurality of inlet ports.

2. The surgical irrigation and suction apparatus of claim 1, wherein the flow of the irrigation fluid through the irrigation tube and the flow of the waste slurry through the suction tube are independently controllable via thumb actuation of a respective pinch valve corresponding to each of the irrigation tube and the suction tube, respectively.

3. The surgical irrigation and suction apparatus of claim 2, wherein each of the respective pinch valves corresponding to the irrigation tube and the suction tube is configured to adjust the corresponding flow through a movement relative to the hollow housing.

4. The surgical irrigation and suction apparatus of claim 2, wherein each of the respective pinch valves corresponding to the irrigation tube and the suction tube, respectively, includes a plurality of discrete flow settings and a setting that entirely shuts off flow to the respective tube.

5. The surgical irrigation and suction apparatus of claim 1, wherein the suction chamber and the irrigation chamber form a single rigid partitioned tube comprising the removable tube.

6. The surgical irrigation and suction apparatus of claim 5, wherein the single rigid partitioned tube is formed from a single extruded or molded piece of plastic.

7. The surgical irrigation and suction apparatus of claim 1, wherein the surgical irrigation and suction apparatus is disposable.

8. The surgical irrigation and suction apparatus of claim 1, wherein the surgical irrigation and suction apparatus is for use in abdominal surgery.

9. The surgical irrigation and suction apparatus of claim 1, wherein the handle of the hollow housing allows a surgeon's hand to grasp the surgical irrigation and suction apparatus so as to manipulate the directionality of the irrigation fluid and the intake of the waste slurry.

10. The surgical irrigation and suction apparatus of claim 1, wherein:

at least one of the respective inlet ports for recovery of the waste slurry is arranged to produce flow substantially collinear with respect to a distal end of the suction chamber; and at least one of the respective inlet ports for recovery of the waste slurry is arranged to produce flow substantially perpendicular with respect to the distal end of the suction chamber.

11. The surgical irrigation and suction apparatus of claim 1, further including:

an irrigation inlet port for coupling the irrigation tube with a source of pressurized irrigation fluid; and a suction outlet port for coupling the suction tube with an external suction pump to collect the waste slurry.

12. The surgical irrigation and suction apparatus of claim 11, wherein the irrigation inlet port and the suction outlet port are housed in or mounted on the handle of the hollow housing.

13. The surgical irrigation and suction apparatus of claim 1, wherein the removable tube is between ten and twenty-five centimeters (cm) in length.

14. The surgical irrigation and suction apparatus of claim 1, wherein the hollow housing comprises two molded pieces of plastic, each forming half of the housing and coupled with one another.

15. The surgical irrigation and suction apparatus of claim 1, wherein the tube fitting is a barbed Wye ("Y") tube fitting partitioned into two branches so as to keep the irrigation fluid from the irrigation chamber separate from the waste flurry from the suction chamber.

16. The surgical irrigation and suction apparatus of claim 1, wherein the removable tube is divided unevenly into the irrigation chamber and the suction chamber by the separator within the tube along the longitudinal direction of the removable tube such that the irrigation chamber is smaller than the suction chamber.

17. A surgical irrigation and suction apparatus, comprising:

a hollow housing forming a handle and a barrel, wherein the hollow housing contains a suction tube for disposing of waste slurry and an irrigation tube for provision of irrigation fluid;

a removable tube divided into an irrigation chamber and a suction chamber by a separator within the tube along a longitudinal direction of the removable tube, wherein the two chambers are collinearly arranged with respect to each other, and the removable tube is coupled with the hollow housing via a tube fitting such that the suction chamber is coupled with the suction tube to form a suction conduit for transporting waste slurry and the irrigation chamber is coupled with the irrigation tube to form an irrigation conduit for transporting irrigation fluid; and an inlet/outlet tip coupled with the removable tube, wherein the inlet/outlet tip includes an outlet port and a plurality of inlet ports, respectively;

wherein:

the irrigation chamber terminates distal to the barrel with the inlet/outlet tip arranged to spray the irrigation fluid through the outlet port substantially collinearly with respect to a distal end of the irrigation chamber;

the suction chamber terminates distal to the barrel with the inlet/outlet tip for recovery of the waste slurry through the plurality of inlet ports;

the flow of the irrigation fluid through the irrigation tube and the flow of the waste slurry through the suction tube are independently controllable via thumb actuation of a respective pinch valve corresponding to each of the irrigation tube and the suction tube, respectively;

each of the respective pinch valves corresponding to the irrigation tube and the suction tube is configured to adjust the corresponding flow through a movement relative to the hollow housing; and the movement includes a translation of the pinch valve and a rotation of the pinch valve relative to the hollow housing.

* * * * *